US007343915B2

(12) United States Patent
Addington et al.

(10) Patent No.: US 7,343,915 B2

(45) Date of Patent: Mar. 18, 2008

(54) APPARATUS AND METHOD FOR SELF-INDUCED COUGH CARDIOPULMONARY RESUSCITATION

(75) Inventors: W. Robert Addington, Melbourne, FL (US); Robert E. Stephens, Kansas City, MO (US); Stuart P. Miller, Melbourne Beach, FL (US)

(73) Assignee: Pneumoflex Systems, L.L.C., Melbourne, FL (US)

( * ) Notice: Subject to any disclaimer, the term of this patent is extended or adjusted under 35 U.S.C. 154(b) by 691 days.

(21) Appl. No.: 10/483,697

(22) PCT Filed: Jul. 16, 2002

(86) PCT No.: PCT/US02/22564

§ 371 (c)(1), (2), (4) Date: Jan. 13, 2004

(87) PCT Pub. No.: WO03/008026

PCT Pub. Date: Jan. 30, 2003

(65) Prior Publication Data

US 2004/0172010 A1 Sep. 2, 2004

Related U.S. Application Data

(60) Provisional application No. 60/322,797, filed on Sep. 17, 2001, provisional application No. 60/305,713, filed on Jul. 16, 2001.

(51) Int. Cl.
*A61M 11/00* (2006.01)

(52) U.S. Cl. .......................... 128/203.12; 128/200.23; 128/200.24

(58) Field of Classification Search .......... 128/200.14, 128/200.16, 200.18, 203.12, 200.24, 200.23, 128/204.23, 200.11, 200.12, 203.15, 205.26, 128/205.23, 204.26

See application file for complete search history.

(56) References Cited

U.S. PATENT DOCUMENTS

| | | | | | |
|---|---|---|---|---|---|
| 4,649,911 | A | * | 3/1987 | Knight et al. | 128/200.21 |
| 5,363,842 | A | * | 11/1994 | Mishelevich et al. | 128/200.14 |
| 5,678,563 | A | * | 10/1997 | Addington et al. | 600/529 |
| 5,894,841 | A | * | 4/1999 | Voges | 128/203.12 |
| 6,119,853 | A | * | 9/2000 | Garrill et al. | 206/204 |
| 6,148,815 | A | * | 11/2000 | Wolf | 128/205.23 |
| 6,758,338 | B2 | * | 7/2004 | Lien | 206/534 |
| 6,958,691 | B1 | * | 10/2005 | Anderson et al. | 340/539.12 |
| 6,981,499 | B2 | * | 1/2006 | Anderson et al. | 128/200.23 |
| 2005/0203349 | A1 | * | 9/2005 | Nanikashvilli | 600/300 |

* cited by examiner

*Primary Examiner*—Steven O. Douglas
(74) *Attorney, Agent, or Firm*—Allen, Dyer, Doppelt, Milbrath & Gilchrist, P.A.

(57) ABSTRACT

A apparatus and method for self-treatment of cardiac arrhythmia by a patient, comprising a container sized to be portable by the patient and having therein a chamber containing a medicament composition comprising a pharmaceutically acceptable carrier mixed with a chemoirritant, preferably L-tartaric acid; a nebulizing valve connected to the chamber so as to provide an outlet therefor; a source of motivating force connected with the chamber so as to motivate the composition through the opening in the nebulizing valve to thereby cause nebulization of the composition; a wireless transmitter responsive to activation of the nebulizer for sending a wireless signal requesting medical assistance; and a power source operatively connected for providing power; wherein the chemoirritant is mixed in the composition in an amount sufficient for causing the patient to produce an involuntary cough effective to maintain at least partial blood circulation.

13 Claims, 3 Drawing Sheets

```
                ┌─────────────┐
                │    START    │─── 10
                └──────┬──────┘
                       │
         ┌─────────────┴─────────────┐
         │   PREPARING COMPOSITION   │─── 12
         └─────────────┬─────────────┘
                       │
         ┌─────────────┴─────────────┐
         │   NEBULIZING COMPOSITION  │◄─── 14
         └─────────────┬─────────────┘
                       │
    ┌──────────────────┴──────────────────┐
    │  DELIVERING NEBULIZED COMPOSITION   │─── 16
    │  TO PATIENT'S UPPER RESPIRATORY     │
    │  TRACT SO AS TO INDUCE COUGH        │
    └──────────────────┬──────────────────┘
                       │
              ┌────────┴────────┐
              │   MONITORING    │─── 18
              │    PATIENT'S    │
              │  HEART RHYTHM   │
              └────────┬────────┘
                       │
                     ╱   ╲
                   ╱  20   ╲
                 ╱  NORMAL   ╲  NO
                ╱   CARDIAC    ╲─────────┐
                ╲   RHYTHM?   ╱          │
                 ╲           ╱           │
                   ╲       ╱             │
                     ╲   ╱              (back to 14)
                      │
                     YES
                      │
                ┌─────┴─────┐
                │   STOP    │─── 22
                └───────────┘
```

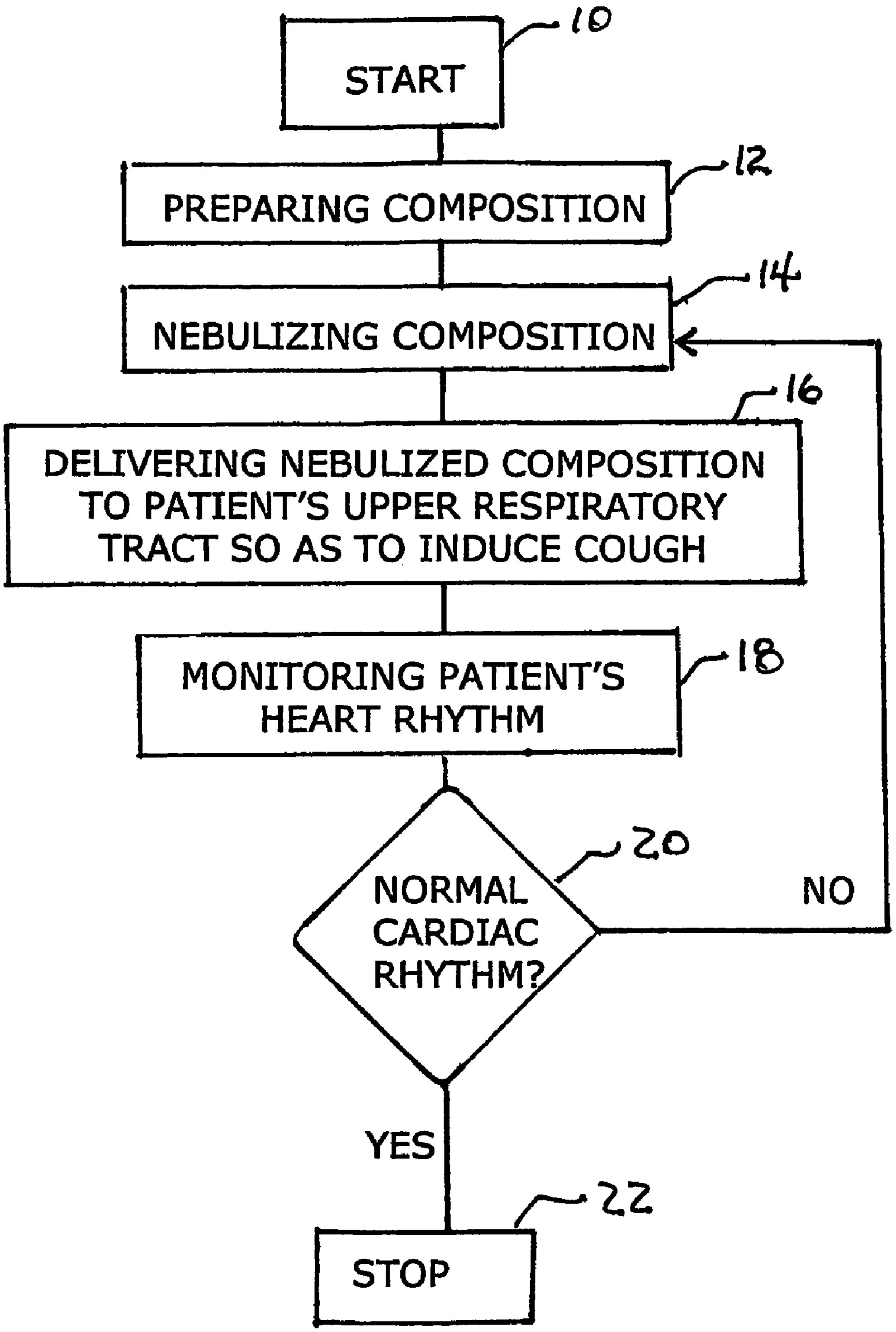

FIG. 1

APPARATUS AND METHOD FOR SELF-INDUCED COUGH CARDIOPULMONARY RESUSCITATION

RELATED APPLICATION

This application claims priority from now abandoned U.S. provisional applications Ser. No. 60/305,713, filed on Jul. 16, 2001, and Ser. No. 60/322,797, filed on Sep. 17, 2001, both of which are incorporated herein by reference in their entireties.

FIELD OF THE INVENTION

The present invention relates to the field of cardiac medicine, and, more particularly, to an apparatus and method for treatment of cardiac symptoms, such as arrhythmia or chest pain, by forceful coughing, and particularly to a method suited for self-treatment by a patient.

BACKGROUND OF THE INVENTION

Cardio pulmonary resuscitation (CPR) has been established since the 1960s as an effective means of helping maintain some circulatory flow in a patient having cardiac arrest. The exact mechanism by which CPR exerts its beneficial effect has been debated over the years, however. It was thought that CPR depended on compression of the heart by externally applied pressure on the chest. Another view holds that CPR is effective through pressure generated upon the pulmonary blood pool as the patient's chest is being manually compressed.

More recently, it has been recognized that a forceful cough brings about violent muscular movements in the chest and diaphragm sufficient for causing an effect similar to that produced by the standard CPR. According to the Merck Manual, coughing is also thought to induce an electrical impulse to the heart, which may help interrupt an otherwise fatal arrhythmia. The cough by the patient leads to generation of an electrical stimulus delivered to the heart, and is also known as a "vagal maneuver" which is voluntary. The cough technique has also been labeled in the literature as "cough CPR" (also CCPR).

In the past twenty years, the medical literature has come to recognize CCPR as a viable method for maintaining some blood circulatory flow in a patient having cardiac arrhythmia or cardiac arrest (also known commonly as a "heart attack"). Cough-CPR, accomplished by abrupt, forceful voluntary coughing by the patient has been shown to maintain consciousness of the patient through its rhythmic compression of the heart and through initiation of a voluntary vagal maneuver to affect the heart's electrical activity. The method of CCPR has several advantages over external CPR when used in the cardiac catheterization laboratory, and may be applicable to other situations where serious rhythm disturbances are experienced before unconsciousness occurs. Cough-induced cardiac compression or electrical impulse intervention is essentially self-performed by the patient, and compared to external chest compression is less likely to traumatize the chest wall or heart. In addition, CCPR can be performed by the patient in any position and on any surface.

Some medical experts have recommended that patients undergoing coronary arteriography be previously trained to cough abruptly and repeatedly every 1-3 seconds. Nevertheless, these same experts are of the opinion that the potential for utilizing this technique in other circumstances (i.e., CCU, home) is less favorable than during catheterization-induced ventricular fibrillation, perhaps because in the cardiac lab setting the physician is at hand and able to assist the patient. CCPR, however, might also be employed successfully in patients with premonitory symptoms of ventricular arrhythmias or Stokes-Adams seizures. In these cases, the prior training of high risk individuals and their spouses to induce effective coughing in the victim might be lifesaving.

SUMMARY OF THE INVENTION

With the foregoing in mind, the present invention advantageously provides a method and apparatus for self-induced CCPR through the production of a forceful, involuntary cough. The invention essentially comprises an "involuntary vagal maneuver", which is a term coined by the inventors to indicate that the involuntarily produced cough is believed to operate at least partly by generating an electrical impulse delivered to the heart, similar to the vagal maneuver known in the art. The present invention eliminates the training requirement for the patient and, as it is self-induced, and does not require the participation or assistance of any other person. For that reason, the present invention is particularly advantageous for use by patients who may be living alone. Furthermore, the cough, which produces the CCPR, is involuntarily generated through the use of the composition of the invention, thus requiring no action by the patient, other than nebulizing the composition to contact his respiratory tract. Effective nebulizing of the composition may be accomplished through the use of a typical hand-held nebulizer device such as previously used for administration of aerosolized medicaments to asthmatic patients.

BRIEF DESCRIPTION OF THE DRAWINGS

Some of the features, advantages, and benefits of the present invention having been stated, others will become apparent as the description proceeds when taken in conjunction with the accompanying drawings in which:

FIG. 1 is a flow diagram illustrating a treatment method according to an embodiment of the present invention;

DETAILED DESCRIPTION OF THE PREFERRED EMBODIMENT

Figure 2:
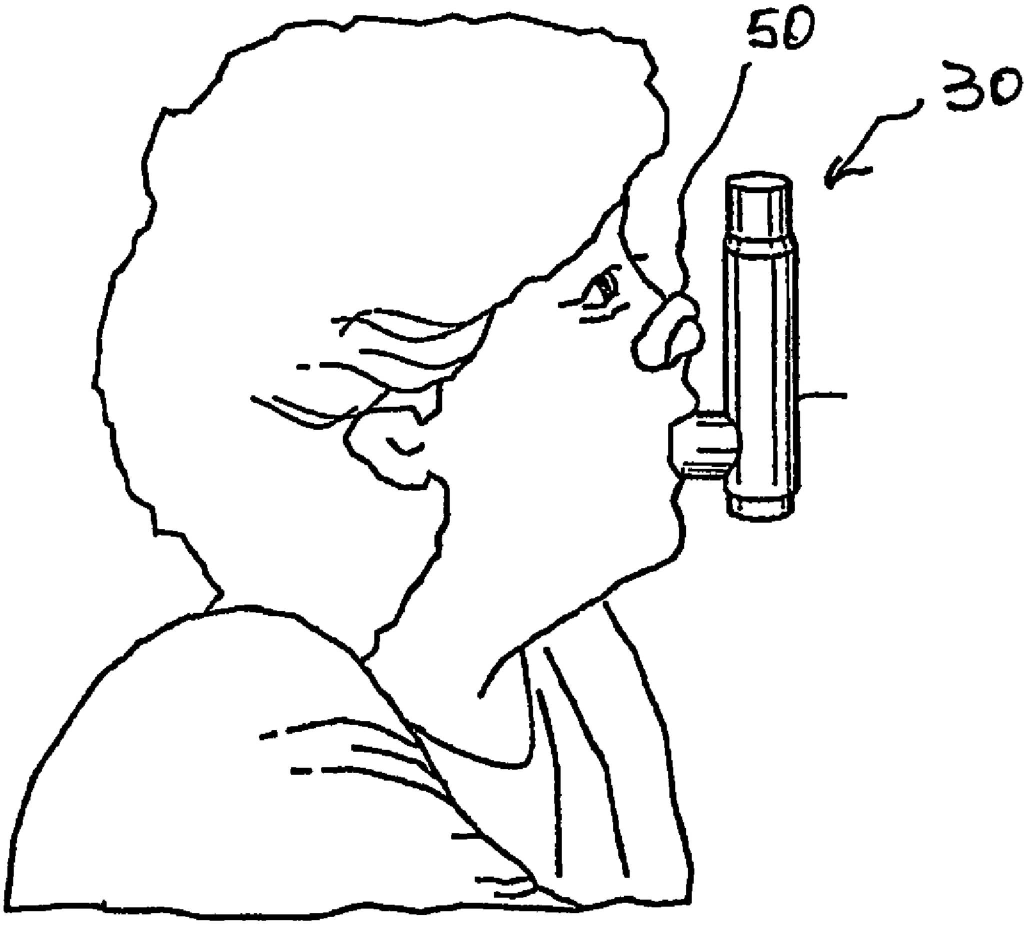
FIG. 2 shows the nebulizer apparatus of the present invention in use.

The present invention will now be described more fully hereinafter with reference to the accompanying drawings, in which preferred embodiments of the invention are shown. This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art.

The present invention advantageously provides a method of self-treatment by a patient experiencing cardiac symptoms, such as cardiac arrhythmia and/or cardiac arrest. The method involves nebulization of a chemoirritant composition delivered to the patient's upper respiratory tract to thereby induce production of an involuntary cough by the patient. Vigorous coughing acts akin to manual chest compression to cause the heart to pump to maintain at least a partial blood circulation in the patient, or to electrically interrupt a potentially fatal arrhythmia via an involuntary vagal maneuver. The invention also provides an apparatus and kit for a patient to self-induce CCPR and to signal a need for medical help.

A preferred embodiment of the invention includes a method of self-treatment in a patient experiencing cardiac symptoms such as arrhythmia by inducing an involuntary cough, the method comprising delivery to the patient's upper respiratory tract of a nebulized composition comprising a pharmaceutically acceptable carrier mixed with chemoirritant effective for causing the involuntary cough. A preferred chemoirritant is L-tartaric acid. As noted above, a forceful cough will act to mechanically compress the heart to thereby aid in maintaining at least a partial blood circulation in the patient during the cardiac arrhythmia, or to electrically interrupt the arrhythmia before it progresses to fatal ventricular fibrillation. The pharmaceutically acceptable carrier in the method preferably comprises, but is not limited to, an aqueous saline solution and a preferred chemoirritant, L-tartaric acid, is substantially soluble therein to form an L-tartrate. Additionally, the pharmaceutically acceptable carrier optionally comprises a solution of sodium chloride, and particularly a solution having at least about 0.15 M sodium chloride. A composition comprising at least about 20% L-tartrate has been found effective in the method, and is offered by way of non-limiting example. Nebulization of the composition for delivery to the patient best comprises droplets having an airborne diameter of about 10 μm or less to promote penetration into the patient's airways, although penetration of the lower airway is not required with L-tartrate as the chemoirritant for production of an involuntary cough, but may depend on the chemoirritant employed. The exemplary solution of 20% L-tartaric acid is preferably nebulized at a rate of about 0.2 ml per minute.

The method of the invention is illustrated in the block diagram shown in FIG. 1. The method begins from the start 10 by preparing the composition 12. The composition is then nebulized 14 and delivered 16 to the patient's upper respiratory tract so as to induce a cough. The patient's cardiac rhythm is monitored 20 during the process. If normal cardia rhythm is restored, the method stops 22. If normal cardiac rhythm has not been restored, nebulizing 14 is repeated and the method continues until normal cardiac rhythm has been restored or medical help becomes available.

A nebulizer apparatus 30, as shown in FIG. 1, is adapted for self-treatment by a patient having a symptoms of cardiac arrhythmia and comprises a container sized to be portable by the patient and having therein a chamber containing a composition including a pharmaceutically acceptable carrier mixed with an effective chemoirritant, preferably L-tartaric acid. The container includes a nebulizing valve, as known in the art, connected to the chamber, a source of pneumatic pressure to motivate the composition through the opening in the nebulizing valve to thereby cause nebulization of the composition, a wireless transmitter, and a power source. As noted above, nebulization preferably comprises droplets having an airborne diameter of less than about 10 μm. Further, the L-tartaric acid is mixed in the composition in an amount effective for causing an involuntary cough by the patient. A preferred pharmaceutical carrier comprises a solution of sodium chloride of at least about 0.15 M sodium chloride. The composition is effectively prepared with at least about 20% L-tartaric acid. The nebulizer apparatus further comprises an outlet positioned in fluid connection with the nebulizing valve and downstream therefrom to thereby convey the nebulized composition for delivery to the upper airway of the patient. A typical outlet is preferably, but is not limited to a mouthpiece for nebulizing into the mouth cavity of the patient.

Figure 3:
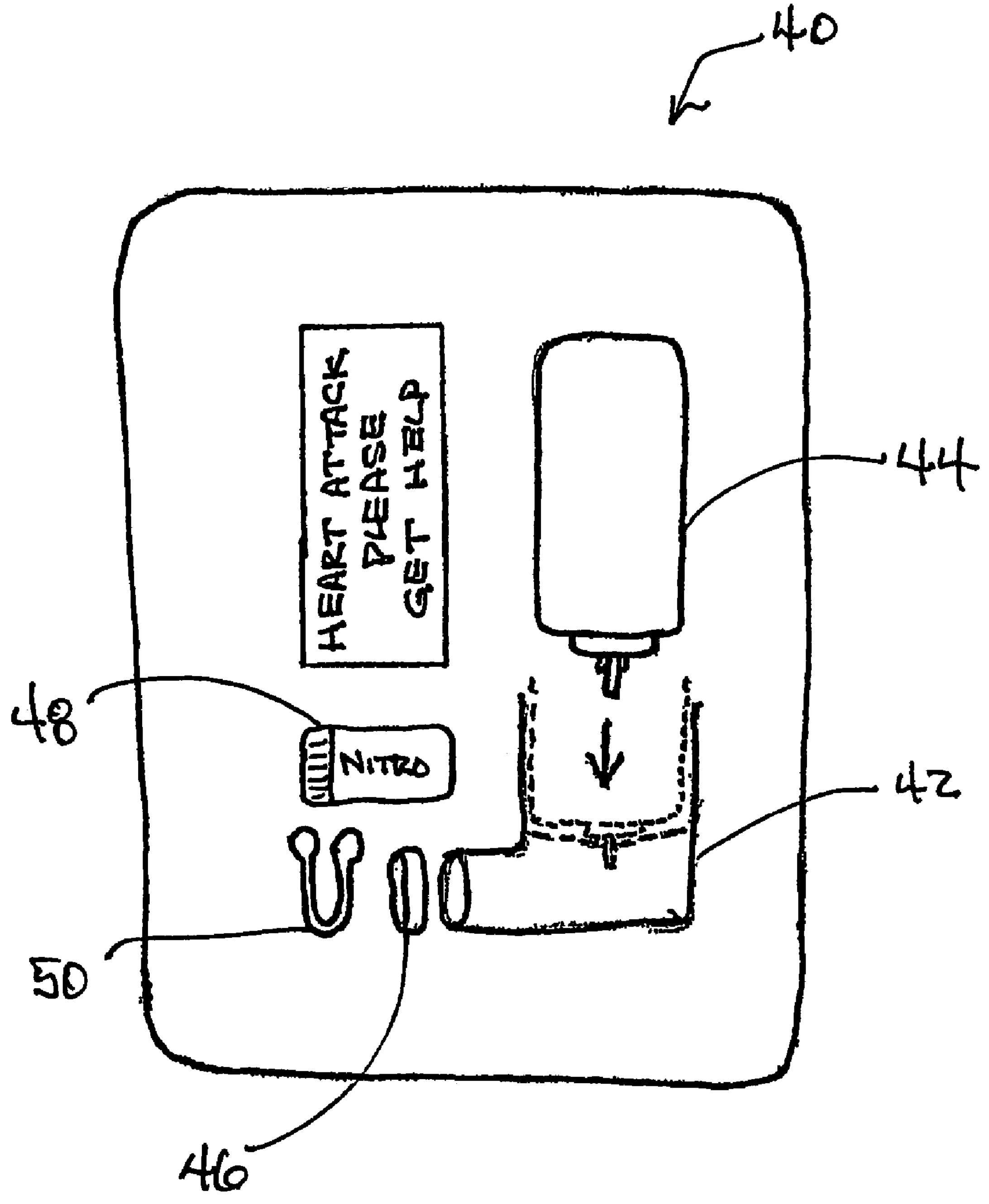
FIG. 3 is a top plan view of a kit comprising the described invention for self-treatment by a patient.

A treatment kit 40, as illustrated in FIG. 3, is adapted for self-treatment by a patient having symptoms of cardiac arrhythmia and comprises a container sized to be portable by the patient and containing a composition comprising a pharmaceutically acceptable carrier mixed with the chemoirritant, preferably L-tartaric acid. The nebulizer is and functions as described above. A housing 42 having an outlet is included in the kit and is connectable to the container 44 so that the outlet is in fluid connection with the nebulizing valve and downstream therefrom to deliver the nebulized composition into a patient's mouth for contacting the upper respiratory tract. Additionally, the kit may also include a removable cap 46 fitting over the outlet. In one embodiment of the invention, the kit further includes at least one nitroglycerin dose 48 for sublingual use by a patient having angina pectoris, or chest pain, which may be present in early cardiac arrhythmias. The kit advantageously may still include a plurality of containers of the composition thereby providing replacements, and a nose clip 50 to close the patient's nose so as to help enhance oral delivery of the composition to the upper respiratory tract. As shown in FIG. 4, the kit preferably also comprises a sign having thereon a notice that the patient is having a heart attack, the sign including an adhesive for attachment to the patient's clothing.

Additionally, as a particularly advantageous feature, the apparatus includes a wireless transmitter (not shown), preferably operating along cellular telephone frequencies, which is activated responsive to use of the nebulizer. The wireless transmitter may be positioned in the housing wherein the nebulizer container fits, or may be a separate device with which the nebulizer apparatus is operatively connected. When the patient activates the nebulizer, the transmitter will broadcast a wireless signal indicating that the patient requires medical help. Such a nebulizer is also referred to herein as a localizing nebulizer. The signal may go directly to a locally monitored wireless network, or medical emergency operator, such as the widely used "911" emergency telephone system in the U.S. To this effect, the nebulizer apparatus also preferably includes a localizing system such as global positioning to determine patient location, and a sign requesting emergency medical help. Alternatively, the wireless signal monitoring network may determine the originating location of the signal by triangulation or other means used in the act.

In operation, when the patient activates the nebulizer, the wireless transmitter generates a signal which allows determining at least patient location and which may also include, a message requesting emergency medical help. The patient may take advantage of locally available medical emergency telephone access, or may participate in a private fee-based monitoring service provided for cardiac patients who carry the apparatus of the present invention. Accordingly, the present invention further includes such a private for-profit monitoring service working in combination with the described apparatus and method of treatment.

The skilled will understand that a hand-held, portable nebulizer permitting location identification may be useful not only with cardiac patients, but also in other emergencies. A person carrying such a nebulizer could activate the device in order to summon help in circumstances unrelated to a medical emergency, for example, in a kidnapping, in a building collapse during an earthquake, etc. Given those advantageous uses, the present invention further includes the localizing nebulizer itself, and an accompanying monitoring network.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims. For example, those skilled in the art will recognize that the present invention may be advantageous not only in self-treatment by a patient, but may also be used by a physician or nurse in the treatment of cardiac arrhythmia of a patient in a medical facility, or may be used by emergency medical technicians and/or firefighters in the treatment of victims experiencing cardiac arrhythmias.

That which is claimed:

1. A nebulizer apparatus for self-treatment of cardiac arrhythmia by production of an involuntary cough in a patient, comprising:

a container sized to be portable by the patient and having therein a chamber containing a medicament composition comprising a pharmaceutically acceptable carrier mixed with a chemoirritant effective for stimulating the patient to produce an involuntary cough;

a nebulizing valve connected to said chamber so as to provide an outlet therefore;

a source of motivating force connected with said chamber so as to motivate said composition through the opening in said nebulizing valve to thereby cause nebulization of said composition;

a wireless transmitter responsive to activation of the nebulizer for sending a wireless signal requesting medical assistance; and a power source operatively connected for providing power; wherein nebulization comprises droplets having an airborne diameter of less than about 10 μm, and wherein the involuntary cough is effective to maintain at least partial blood circulation in the patient.

2. The nebulizer apparatus of claim 1, wherein said chemoirritant comprises L-tartaric acid.

3. The nebulizer apparatus of claim 1, wherein said pharmaceutically acceptable carrier comprises a solution of sodium chloride.

4. The nebulizer apparatus of claim 1, wherein said wireless transmitter further comprises transmission of a wireless signal having a cellular telephone signal frequency.

5. The nebulizer apparatus of claim 1, wherein said wireless signal further comprises information for identifying the patient's location responsive to activation of the nebulizer to thereby summon aid.

6. The nebulizer apparatus of claim 1, wherein said wireless transmitter comprises a wireless signal including patient location information.

7. The nebulizer apparatus of claim 1, in combination with a wireless monitoring network for detecting said signal and responsive thereto for dispatching medical assistance to the patient's location.

8. A treatment kit for self-treatment of cardiac arrhythmia by a patient, said kit comprising:

a nebulizer apparatus including a container sized to be portable by the patient and having a chamber containing a medicament composition comprising a pharmaceutically acceptable carrier mixed with chemoirritant effective for causing an involuntary cough sufficient to maintain at least partial blood circulation in the patient, a nebulizing valve connected to said chamber, a source of pneumatic pressure motivating said composition from the chamber through the nebulizing valve to cause nebulization of said composition, a wireless transmitter responsive to activation of the nebulizer for sending a wireless signal for requesting medical assistance, a location determining system connected for locating the origin of said wireless signal, and a power source operatively connected for providing power to said wireless transmitter; and an outlet connectable to said container so as to be in fluid connection with said nebulizing valve and downstream therefrom for delivering the nebulized composition into contact with the patient's upper respiratory tract.

9. The treatment kit of claim 8, further comprising a plurality of containers thereby providing replacements.

10. The treatment kit of claim 8, further comprising a nose clip.

11. The treatment kit of claim 8, further comprising a sign having thereon a notice that the patient is having a heart attack.

12. The treatment kit of claim 11, wherein the sign is self-adhesive so as to allow the patient to thereby post the sign on his clothing.

13. The treatment kit of claim 8, further comprising at least one dose of nitroglycerin effective for sublingual administration to the patient for treating cardiac chest pain.

* * * * *